United States Patent
Mizzer et al.

[11] Patent Number: 6,118,541
[45] Date of Patent: *Sep. 12, 2000

[54] METHOD TO DETERMINE THE EFFECTIVENESS OF A CHEMICAL MIXING SYSTEM

[75] Inventors: John Paul Mizzer; Ching-Cherng Lee, both of Newark, Del.

[73] Assignee: Dade Behring Inc., Deerfield, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 09/060,034

[22] Filed: Apr. 13, 1998

[51] Int. Cl.[7] ............................................. G01N 21/00
[52] U.S. Cl. ................................. 356/432; 356/320
[58] Field of Search .................... 356/432, 320, 356/300, 39; 436/34, 45, 50, 164; 422/64; 435/805, 18; 73/64.43

[56] References Cited

U.S. PATENT DOCUMENTS

| | | |
|---|---|---|
| 4,145,143 | 3/1979 | Fontaine . |
| 4,299,487 | 11/1981 | Sengoku et al. ............... 356/320 |
| 4,388,474 | 6/1983 | Tanihara . |
| 4,603,154 | 7/1986 | Luetzelschwab . |
| 4,612,289 | 9/1986 | Furuta et al. .................. 436/34 |
| 4,740,460 | 4/1988 | Sataka et al. ................. 435/18 |
| 4,863,693 | 9/1989 | Howell . |
| 5,128,103 | 7/1992 | Wang et al. . |
| 5,216,409 | 6/1993 | Ament et al. . |
| 5,854,011 | 12/1998 | Chen et al. . |
| 5,946,088 | 8/1999 | Aldridge . |

*Primary Examiner*—Frank G. Font
*Assistant Examiner*—Tu T. Nguyen
*Attorney, Agent, or Firm*—Leland K Jordan

[57] ABSTRACT

Confirming sufficient mixture uniformity between a reagent and liquid sample experiencing a kinetic reaction by comparing the amount of light absorbed within the mixture after the reaction begins with the amount of light absorbed within the solution at the completion of the reaction and requiring that the difference between measured amounts of absorbed light be less than a predetermined value.

17 Claims, 5 Drawing Sheets

METHOD TO DETERMINE THE EFFECTIVENESS OF A CHEMICAL MIXING SYSTEM

FIELD OF THE INVENTION

The present invention relates to an automated chemical analyzer for assaying liquid biological samples. In particular, the present invention provides a method to determine if a desired degree of mixing uniformity between liquid laboratory reagents and a patient sample is achieved prior to a final chemical analysis of the sample.

BACKGROUND OF THE INVENTION

In the analytical and diagnostic fields there is a need to uniformly mix liquid laboratory reagents and a patient sample during and prior to chemical analysis and it is known that ultrasonic energy may be used to successfully provide such mixing. The source of ultrasonic energy is typically an ultrasonic horn, a relatively elongated member which vibrates at an ultrasonic frequency as a result of a conversion of an electrical excitation signal into a mechanical vibration. In use, ultrasonic energy is coupled into a reaction compartment containing the liquid laboratory reagent(s) and patient sample in a solution to be mixed resulting in the creation of relatively high sonic energy zones within the composition. Unfortunately, experience has shown that ultrasonic mixing of such a composition may be inadequate for various reasons including too little energy, too short a mixing time, or an improperly shaped mixing vessel. In these instances, inadequate mixing may result in zones of non-uniformity within the liquid solution (sample and reagents) to be analyzed and impart an unwanted degree of inaccuracy during chemical analysis. One approach to this problem is to provide ultrasonic mixing for a period of time in excess of a minimum time predetermined to achieve the desired degree of uniformity, however, such an approach has an adverse impact on throughput. Accordingly, it would be advantageous to provide a method to determine whether the mixing energy applied to a solution within a vessel has produced the desired uniformity of mixing of the sample with liquid reagents. If not, non-homogenous solution zones may remain therein, in which event, an operator may be alerted to prevent an otherwise undetectable adverse impact upon the accuracy of a reported sample analysis.

SUMMARY OF THE INVENTION

The present invention provides a method to determine if a desired degree of uniformity of mixing of chemical reagents and a liquid sample has been achieved by measuring a first amount of light absorbed when transmitted through a vessel containing a mixed solution of sample and reagent at a predetermined amount of time before a final sample analysis measurement is made. The first amount of absorbed light is compared to a second amount of light absorbed when transmitted through the vessel at the time that a final sample analysis measurement is made. It has been discovered that if the ratio between the first and second amounts of absorbed light is greater than a predetermined percentage, adequate mixing of the sample has occurred.

DETAILED DESCRIPTION OF THE INVENTION

Figure 1:
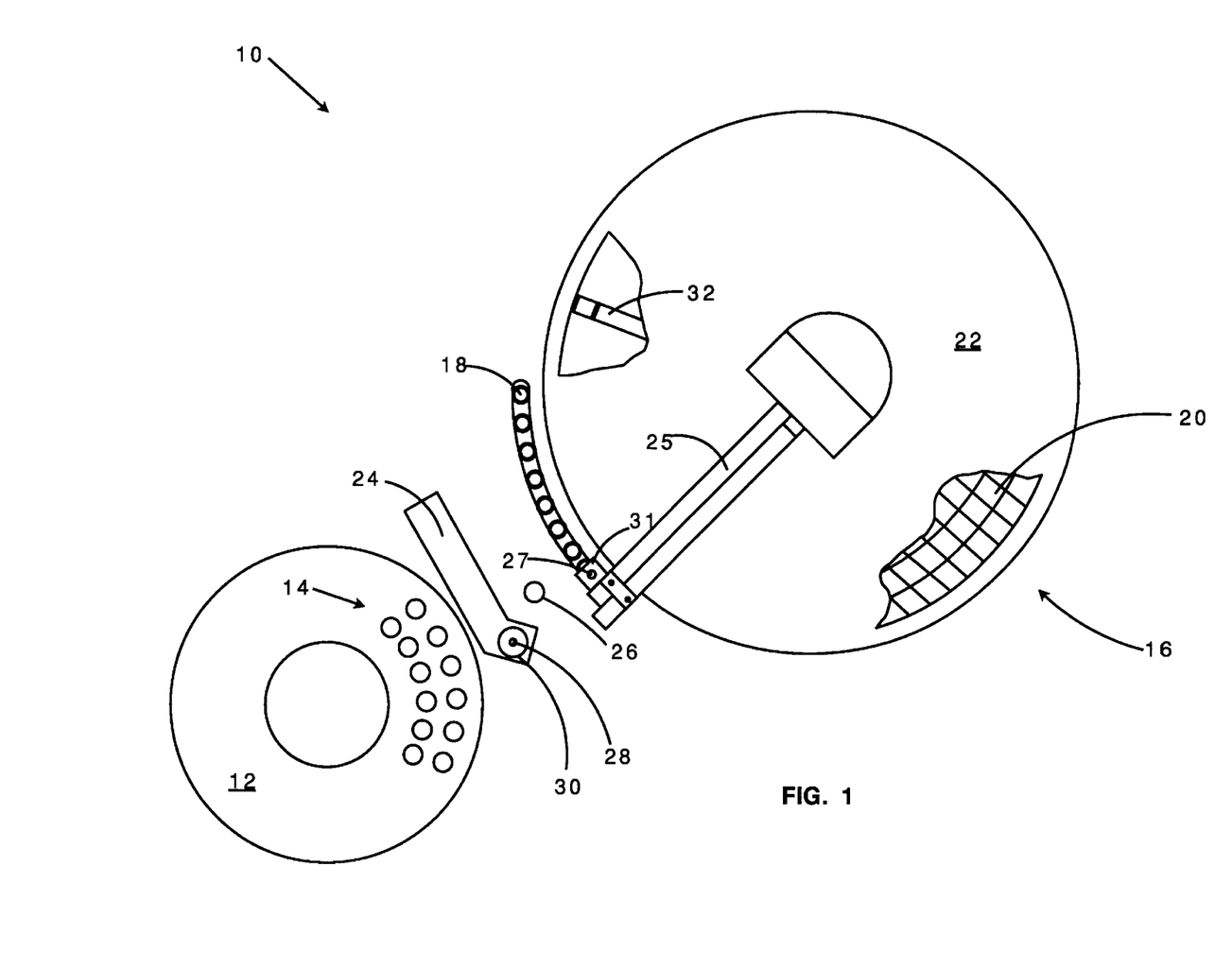
FIG. 1 is a schematic plan view of an automated analyzer in which the present invention may be used to advantage.

FIG. 1 shows schematically the elements of a conventional automatic chemical analyzer 10 comprising a sample cup carousel 12 supporting a plurality of sample cups 14, a cuvette carousel 16 adapted to receive a plurality of reaction vessels or cuvettes 18, and a plurality of reagent liquid cartridges 20 illustrated as disposed beneath a cut out portion of a lid 22 which covers various thermally controlled areas. Reagent cartridges 20 are preferably a multi-compartment container such as those sold under the tradename FLEX™ by Dade Behring Inc., Newark, Del. Reaction cuvettes 18 are formed by pulling two different composition ribbons of clear film from a cuvette film cartridge, not shown, onto the periphery of the cuvette carousel 16. The cuvette carousel 16, preferably in the form of a wheel, has about one hundred separate cuvettes 18, the inner wall of each cuvette 18 having an opening to allow transmission of light. A small opening remains at the top of the cuvette 18 to allow the addition of reagent liquid and sample liquid. A sample liquid arm 24 and a wash resource 26 are located proximate the sample cup carousel 12 and cuvette carousel 16. Sample liquid arm 24 supports a conventional sample liquid probe 28 and an ultrasonic mixing mechanism 30 and is mounted to a rotatable shaft so that movement of sample liquid arm 24 describes an arc intersecting the three components 14, 18, and 26. Details may be found in U.S. Pat. No. 4,863,693, assigned to the assignee of the present invention and incorporated herein by reference.

A liquid reagent arm 25 is mounted above cuvette carousel 16 for relative rotational movement with respect thereto to provide the capability to randomly dispose reagent arm 25 at any selected angular location above cuvette carousel 16. Liquid reagent arm 25 also supports a conventional reagent liquid probe 27 adapted to draw reagent liquid from an appropriate reagent liquid cartridge 20 and deposit reagent liquid within a predetermined cuvette 18. Probe 27 further comprises an ultrasonic mixing mechanism 31 included for hydrating, aspirating, dispensing and mixing reagents. Each of the ultrasonic mixing mechanisms 30 and 31 include a horn portion having an elongated shape and an associated pair of piezoelectric crystals and appropriate electronics. The frequencies of oscillation are made to be coincident with the natural parallel resonant frequency of the ultrasonic mechanisms 30 and 31. Details of construction of the mixers are known in the art and typically comprise a half-wavelength ultrasonic sample piezoelectric transducer mounted by O-rings into reagent arm 25 and sample arm 24 and a half-wavelength tip that is attached to the transducer body by a coupling nut. The tip and transducer body contain an axial liquid passage that exits in a right angle tube fitting port in the transducer body. A pair of motors may be employed to rotate reagent arm 25 and translate it vertically so that the reagent arm 25 may access any one of the cuvettes 18.

To perform the ultrasonic mixing functions, piezoceramic disks, for example comprising lead zirconate-titanate (PZT) piezoelectric ceramic disks, are electrically driven to vibrate the mixing assembly 30. The transducer, nut, and tip form a tuned mechanical assembly designed to vibrate at a frequency near its longitudinal natural frequency. The electronic drive circuit matched with this transducer is designed to resonate the assembly longitudinal natural frequency and uses a phase-feedback circuit to maintain the resonance frequency. Drive voltage levels are selected to obtain tip vibration amplitude levels and these are determined by the piezoelectric constant and capacitance of the piezoceramic disks, for example, a drive voltage in the 300–400 volt range has been used to obtain a 2 to 3 mil peak-to-peak tip amplitude vibration amplitude, with the exemplary PZT disks having a piezoelectric constant in the range about $200 \times 10^{-9}$ m/v and a capacitance of about 1250 pf measured at a frequency of 1 kHz.

A reaction monitoring device 32, such as a photometer, is disposed beneath the cuvette carousel 16 and mounted by a conventional drive motor for independent rotational movement with respect thereto. Reaction monitoring device 32 typically comprises a source of a radiation light beam, various lenses, a filter wheel assembly driven by a suitable drive motor and a photodetector mounted adjacent to the outer periphery of a cuvette 18. A system such as that described in U.S. Pat. No. 5,128,103 and assigned to the assignee of the present application is preferably employed. An interrogating light beam of radiation passes through the various lenses and is focused through a selected filter in the wheel and is then directed by a mirror through the inner wall of each cuvette 18 toward the photodetector. In a commercially available embodiment, ten filters are provided having nominal radiation transmissions centered within +3 nm at wavelengths of 293, 340, 383, 405, 452, 510, 540, 577, 600, and 700 nm and bandwidths at half-peak of less than 12 nm. Voltage output from the photodetector is directly proportional to the amount of incident radiation at the filtered wavelength.

Because of the described constructional relationship, the instrument 10 in accordance with the present invention is capable of advantageously measuring light absorbance occurring at various wavelengths during transmission of light through the reaction fluid contained the reaction cuvette 18, thereby monitoring the reaction occurring in any cuvette 18 disposed at any predetermined point on the cuvette carousel 16. Thus, at any point in time during the assay process, including before addition of reagent liquids to the cuvette 18, after addition of reagent liquids to the cuvette 18, after addition of sample liquids to the cuvette 18 continuing liquid reagents, during mixing of reagent and sample liquids within the cuvette 18, light absorbance occurring as a result of a chemical reaction may be photometrically determined in addition to light absorbance determined at a time when the solution within the cuvette 18 reaches a predetermined final end point stage. In making such photometric measurements, reaction monitoring device 32 measures the resulting absorbance or turbidity of the solution contained in cuvette 18 using well known analytical procedures. Photometric readings are supplied to a computer where the readings may be converted using well known techniques into analyte concentration units and displayed or recorded.

A combination of liquids, generally sample and reagent plus other liquids to be mixed uniformly may be introduced into the cuvette 18 using sample arm 24 and reagent arm 25, respectively. Most frequently, a reagent liquid solution is initially dispensed into a cuvette 18 using reagent probe 27 and mixed using ultrasonic energy provided from the ultrasonic mechanism 31 attached to reagent arm 25 as reagent arm 25 is lowered into cuvette 18. Actuation of ultrasonic mechanism 31 introduces ultrasonic energy into the solution within cuvette 18 and directs the energy substantially axially of the cuvette 18 to generate a relatively high ultrasonic energy region within the cuvette 18 in which the liquids to be mixed are confined. The ultrasonic energy may be applied continuously or in bursts, with a relatively constant or varying frequency.

Subsequent to reagent mixing within cuvette 18, a sample liquid solution is dispensed into cuvette 18 using sample probe 28 and mixed using ultrasonic energy provided from the ultrasonic mechanism 30 attached to sample arm 24. Actuation of ultrasonic mechanism 30 generates a similar high ultrasonic energy region within the cuvette 18 in which the liquids to be mixed are confined. As a result of the confinement of the sample and reagents to the high energy zone, high speed mixing of the liquids due to the application of ultrasonic energy is achieved. Times of mixing of the sample and reagents of less than one second are possible.

In the case of endpoint reaction analysis measurement techniques, it has been discovered that the sufficiency of uniformity of ultrasonic mixing for achieving analytically correct measurement results may be determined by relating the reaction absorbance (RA) at a time whereat about 50–70% of the reaction time is completed to the reaction absorbance at a later final time when the reaction is completed, a time generally known as the reaction endpoint. Such endpoint techniques typically monitor the presence of a tag having a concentration related to the analyte concentration or monitoring the photometric absorption properties of the analyte as the analyte is converted to a non-photometric absorbing entity due to presence of an enzyme or the like. The tag is generated during a chemical reaction between sample suspected of containing an analyte and various reagents. It is critically important to produce adequate uniformity of mixing between sample and the reagents elsewise the amount of tag or the extent of conversion to a non-absorbing entity may not accurately represent the amount of analyte present in the sample. The following two examples illustrate the present invention.

A first exemplary example of this technique for ascertaining the uniformity of mixing involves an assay in which absorption increases during the measurement procedure, an assay generally known as a "positive absorption" assay. An example of such a "positive absorption" assay is a measurement to determine the amount of glucose in a sample using a procedure employing enzymes to increase specificity, typically using either glucose oxidase or hexokinase reactions. The hexokinase method involves two coupled reactions in which hexokinase catalyzes the phosphorylation of glucose by adenosine-5'-triphosphate (ATP) to glucose-6-phosphate which is oxidized to 6-phosphogluconolactone by glucose-6-phosphate dehydrogense (G-6-PDH) with simultaneous reduction of nicotinamide-adenine dinucleotide phosphate (NADP). NADP is reduced to NADPH and the glucose concentration is determined using a known bichromatic endpoint technique.

Figure 2:
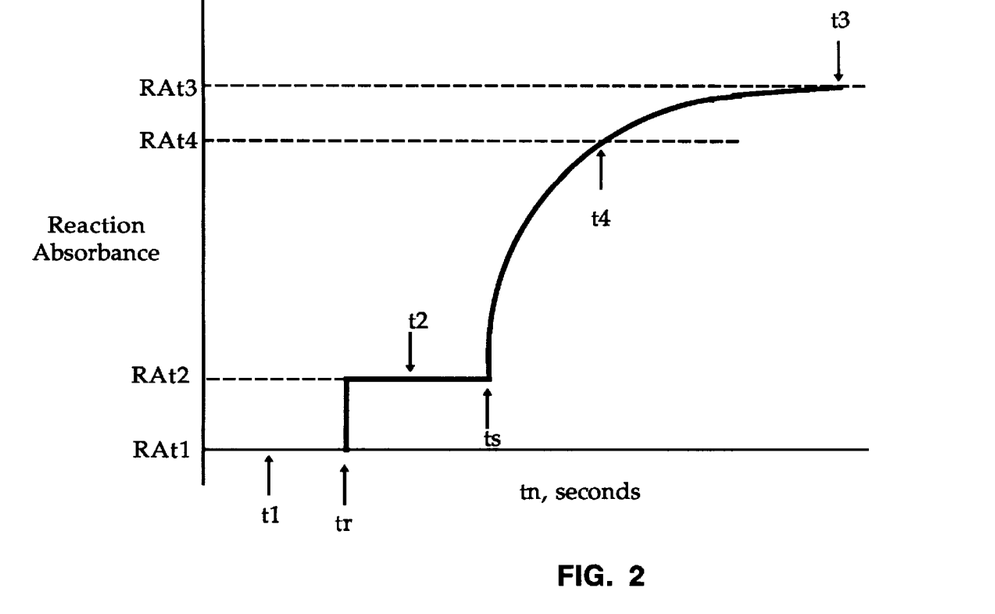
FIG. 2 is a graphical representation of a first type endpoint analytical assay having analytically sufficient mixing.

In such an exemplary assay, illustrated in FIG. 2, analytical measurements begin with an initial RAt1 reading at time t1 of absorbance through a cuvette 18 prior to introduction of liquids and reagents thereinto so as to provide a pair of "baseline" reaction absorbance measurements, RA, made at two wavelengths, $\lambda 1$ and $\lambda 2$, the first wavelength, $\lambda 1$, chosen to be characteristic of the tagged byproduct of the reaction of the sample and reagents within cuvette 18, and the second wavelength, $\lambda 2$, chosen to be characteristic of the cuvette 18 and potential interfering substances within the cuvette 18 and/or optical measurement discrepancies that may exist between the light source, cuvette and photodetectors. The second wavelength, $\lambda 2$, is popularly known as a "blanking wavelength", and is primarily characteristic of the analytical system being employed. In this exemplary example, for a glucose analysis using NADPH as a tag, the first wavelength, $\lambda 1$, chosen to be attributable to the reaction, is known to be at about 340 nm and the second wavelength, $\lambda 2$, is selected to indicate non-analyte related absorption, typically at about 383 nm. As used herein, RAtn is equal to the difference between a reaction absorbance measurement, RAtn($\lambda 1$), measured at $\lambda 1$ and a reaction absorbance measurement, RAtn($\lambda 2$) measured at $\lambda 2$, where t identifies the time of the respective measurement.

A few seconds after t1, usually between 10 and 30 seconds later, at a time tr, known volumes of reagents and purified water are introduced into the cuvette 18. FIG. 2 shows the effect upon monitored reaction absorption as being a sharp increase at the time of addition of the reagents and water. In the instance of assays having a rate controlled by kinetic principles, ultrasonic mixing is known to be effective in providing a high degree of mixing uniformity. It has been experimentally determined that ultrasonic mixing of reagent and water, using an ultrasonic mixer 31 having conventional structure like that described hereinbefore using pulsed applications of ultrasonic energy produces analytically correct results. Typically, ultrasonic mixing is conducted over a period of about one second in a uniformly spaced series of ten 30 msec pulsed applications of ultrasonic energy using a voltage level of 325 volts (ac), as powered by a self resonant power supply network.

Sample addition into the cuvette 18 is next made at time ts about 30 seconds after t2 using sample probe 28, as illustrated in FIG. 2, wherein sample probe 28 comprises an ultrasonic mixer 30 having conventional structure like that described hereinbefore using pulsed applications of ultrasonic energy determined to produce analytically correct results. The effect upon reaction absorption RA in a "positive absorption" assay is observed as an increasing photometric absorption following addition of the sample to previously mixed reagent(s) and water. In assays regulated by kinetic principles, sample addition is followed by pulsed ultrasonic mixing. In commercial applications of such a glucose analysis, following sample addition, the sample-reagent(s)-water solution is mixed ultrasonically using ultrasonic mixer 30 for a period of about one-half second in a uniformly spaced series of five 40 msec pulsed applications of ultrasonic energy using a voltage level of 375 volts. When operated at about 375 volts, the average power expended by the ultrasonic mixing mechanism 30 may be determined from voltage and current data to be about 3 watts so that during a 100% duty cycle operation over a period of 0.5 seconds, about 1.5 joules of energy is delivered to the ultrasonic mixer 30. Measurements made on the amount of heat transferred to liquid within a cuvette 18 using ultrasonic mixer 30 indicate that about 30% of the total energy is consumed within internal portions of the ultrasonic mixer 30 and that about 60% of the total energy is transferred to the liquid. A second absorbance measurement RAt2 attributable to the cuvette 18 plus the added reagent(s) and water is made at time t2 at the two bichromatic wavelengths, $\lambda 1$ and $\lambda 2$.

This mixing is followed by an endpoint reaction absorbance measurement, RAt3, attributable to the cuvette 18 plus the assay reagents and water and sample empirically determined to be sufficient to allow the reaction to be essentially fully completed, made at a time t3 about 180 seconds after addition of sample into the cuvette 18 at the two bichromatic wavelengths. In this instance, then, Endpoint Reaction Absorbance is thus defined by Formula 1.

Formula 1: Endpoint Reaction Absorbance=[RAt3−RAt1]−[RAt2−RAt1]

where Reaction Absorption at time RAtn, is defined by RAtn=RAtn($\lambda 1$)−RAtn($\lambda 2$), for time t1, t2, t3, etc.

Because of the presence of additional liquid in cuvette 18 after the addition of sample and water, an endpoint measurement procedure typically employs a volume correction to account for the increased absorption arising from the additional liquid in the cuvette 18 as well as for "background" absorption by the cuvette 18. This is a well-known process and uses a formula such as Formula 2 below:

Background and Volume (B&V) Corrected Endpoint Reaction Absorbance,

Formula 2: RAtn (B&V)=[RAt3−RAt1]−[RAt2−RAt1]×V2/V3 where V2 is the known volume of reagent and water in the cuvette 18 at time t2 and V3 is the known volume of reagent and water plus sample and water in the cuvette 18 at time t3. As used herein, all RA measurements are calculated in a manner to incorporate such a background and volume correction.

Figure 4:
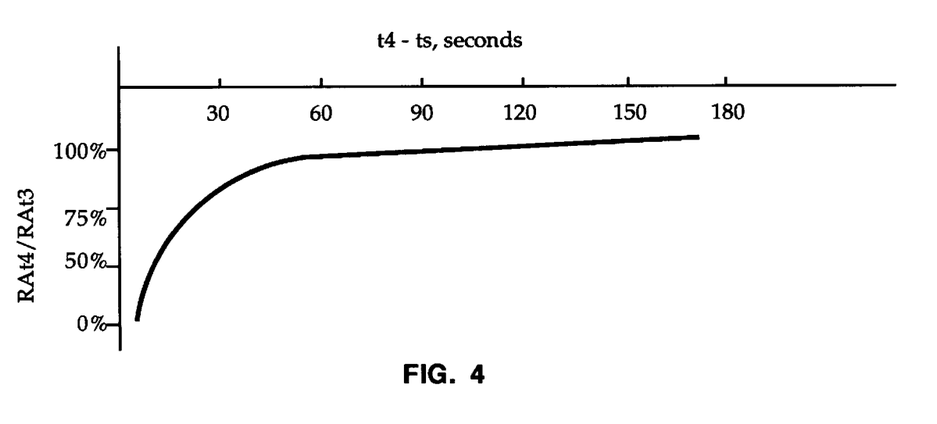
FIG. 4 is a graphical representation of signal absorption ratios typical of sufficient mixing of sample and reagents exemplary of the present invention for the assay of FIG. 2.

The present invention introduces a new reaction measurement, RAt4, at a time after introduction of sample into the cuvette 18 and before the endpoint reaction absorbance measurement, RAt3, so that the relative value of a reaction absorption curve during the reaction may be used in conjunction with the final reaction absorption endpoint value to determine if a sufficient degree of mixing efficiency has been achieved by the ultrasonic mixing process. As illustrated in FIG. 4 and described later, it has been determined that time t4 can be selected within a range so that if the ratio of RAt4 to RAt3 is in a range from about 98% to 102%, then sufficiently uniform mixing of the reagent, water and sample has been achieved so as to yield an analytically acceptable test result. Similarly, it has been determined that time t4 can be selected within a range so that if the ratio of RAt4 to RAt3 is less than about 95%, then insufficiently uniform mixing of the reagent, water and sample has been achieved resulting in an analytically unacceptable test result.

Referring again to FIG. 2, in an exemplary illustration of the present invention, as a kinetically controlled glucose reaction nears an endpoint completion at a time t4 selected to be in the range about 50–70% of the time interval between ts and t3, a new reaction absorption measurement, RAt4 made at time t4, can be compared to the endpoint reaction absorption measurement RAt3 and the difference between the two reaction absorption measurements used to determine the adequacy of mixing of the sample analyzed using reaction absorption measurements. In this example, sample to be analyzed is added to the cuvette at time ts about sixty seconds after tr and this addition is followed by pulsed ultrasonic mixing using mixer 30, in this instance of a glucose assay for a period of about one-half second in a uniformly spaced series of five 40 msec pulsed applications of ultrasonic energy again a voltage level of about 375 volts, the times and ultrasonic energy levels being empirically determined to produce a sufficient uniformity of mixing that will yield "analytically correct measurements". As herein employed, the term "analytically correct measurements" is meant to define instances wherein the mixing of sample and reagents is sufficiently uniform as to have no adverse measurable affects on the accuracy of the assay to be performed.

An end-point absorbance measurement RAt3 attributable to the cuvette 18 plus the reagent(s) and water and sample may then be made at the two bichromatic wavelengths, $\lambda 1$ and $\lambda 2$ at a time t3 of about 180 seconds after ts, the time of sample addition, t3 being empirically determined to be sufficient to allow the reaction to be essentially fully completed after addition of sample into the cuvette 18. It is evident from an inspection of the curve that when determining the Endpoint Reaction Absorbance, the subtracted term [RAt2–RAt1] is representative of absorption due to the cuvette, reagent and water without sample effects.

Figure 3:
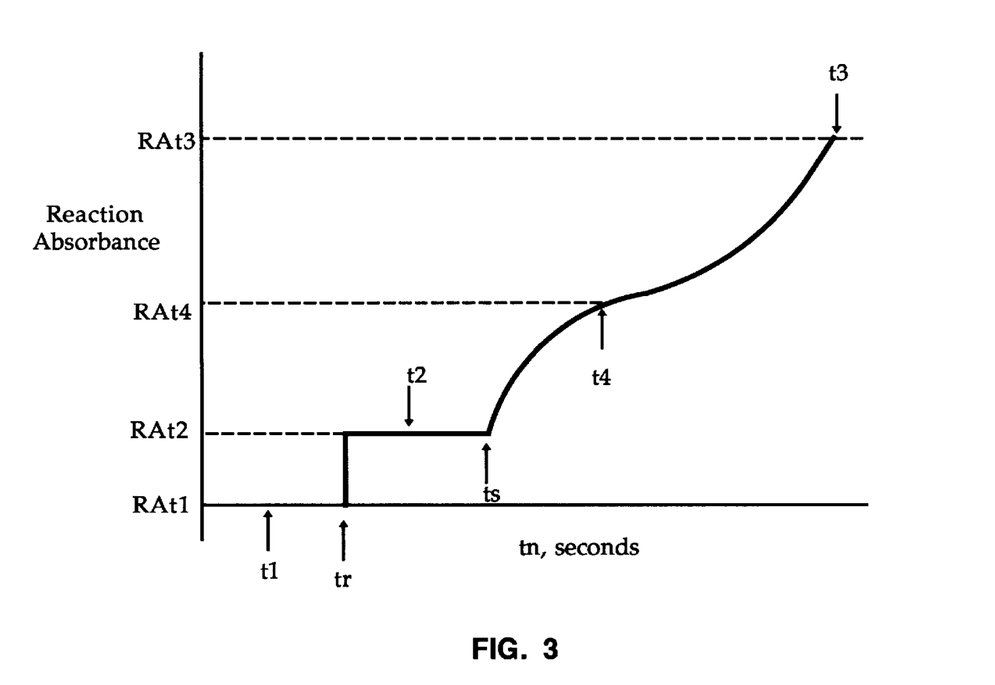
FIG. 3 is a graphical representation of a end-point analytical assay having analytically insufficient mixing.

In contrast, FIG. 3 shows the effect upon reaction absorption RA in a "positive absorption" assay in a "insufficient mixing" situation where the difference between ts and t3 is about 180 sec and when either: (1) no ultrasonic energy was applied by mixer 30 to a reaction solution containing glucose in 300 ul purified water and 56 ul hexokinase, adenosine-5'-triphosphate (ATP) and glucose-6-phosphate dehydrogense G-6-PDH; or when, (2) ultrasonic energy was applied by mixer 30 for one 20 msec pulsed application of ultrasonic energy using a voltage level of 375 volts, an energy level know to be about 10% of the normal level of energy previously determined to produce an analytically acceptable uniformity of mixing.

FIG. 4 shows a series of ratios between RAt3 and RAt4 determined at different time values for t4 in a kinetically controlled "positive absorption" reaction as the reaction nears an endpoint completion at a time t3 under conditions of sufficient ultrasonic mixing to result in analytically correct measurement results. In this reaction, the difference between ts and t3 is about 180 sec and acceptable mixing was performed using the ultrasonic mixing mechanism 30 at a voltage level of 375 volts over a period of about one-half second in a uniformly spaced series of five 40 msec pulsed applications of ultrasonic energy as described hereinbefore and known to produce analytically acceptable mixing. The data were determined on a group of 5 different samples. In this instance, the same series of ratios between RAt3 and RAt4 determined at different times during a reaction show that the ratio between RAt4 and RAt3 at a time t4 within a range of about 50–70% of the endpoint t3 is greater than about 98%.

Figure 5:
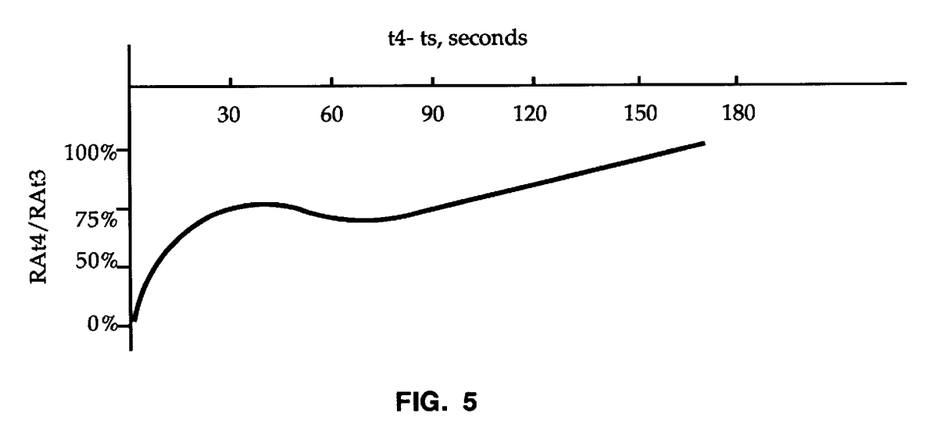
FIG. 5 is a graphical representation of signal absorption ratios typical of insufficient mixing of sample and reagents exemplary of the present invention for the assay of FIG. 3.

In contrast, FIG. 5 shows the series of ratios between RAt4 and RAt3 determined at different time values for t4 for the above described "insufficient mixing" example when either no ultrasonic energy was applied or when an ultrasonic mixing energy level know to be about 10% of the normal level of energy known to produce an analytically acceptable uniformity of mixing. For both of these "weak" mixing instances, the ratio between RAt4 and RAt3 at time t4 is generally found to be less than about 95%. For both of these "weak" mixing instances, it is clear that the ratio between RAt4 and RAt3 at a time t4 within a range of about 50–70% of the endpoint t3 is generally less than about 95%. In some exceptional instances, the ratio between RAt4 and RAt3 has been measured to be higher than about 95% but in these instances, although not fully understood, the measurements are found to have an abnormally large range of values.

A second exemplary example of this technique for ascertaining the uniformity of mixing involves an assay in which the photometric absorption of light transmitted through the reagent(s)-water-sample solution decreases during the assay procedure, generally as a result of loss of an analyte's absorbance properties at a particular wavelength. Such assays are known as a "negative absorption" assays. An example of such a "negative absorption" assay is an in vitro diagnostic assay for the quantitative determination of uric acid in serum, plasma and urine. The assay converts uric acid, which is strongly absorbent at 293 nm, by the purposeful addition of uricase to allantoin, which is non-absorbing at 293 nm. Thus, the amount of negative or decreased absorbance at 293 nm, caused by the disappearance of uric acid, is directly proportional to the original concentration of uric acid in the sample. Such "negative absorption" assays may be performed using a bichromatic endpoint measurement similar to the technique described in the above mentioned glucose assay.

Figure 6:
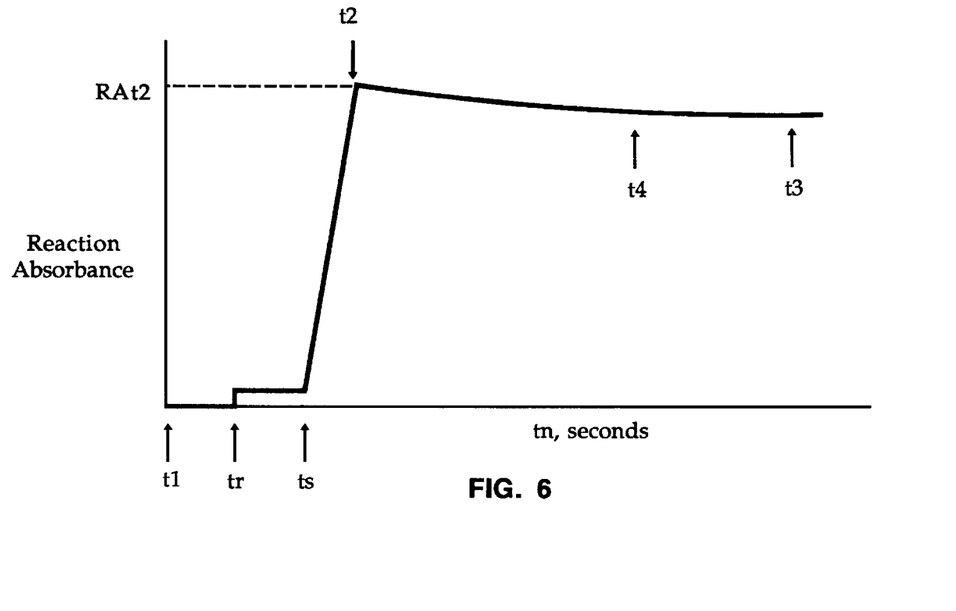
FIG. 6 is a graphical representation of events in a second type of end-point analytical assay having analytically sufficient mixing.

A commercially available "negative absorption" assay, in this instance for uric add, is illustrated in FIG. 6. Again, analytical measurements begin with an initial RAt1 reading at time t1 of absorbance through a cuvette 18 prior to introduction of liquids and reagents thereinto so as to provide a pair of "baseline" absorbance measurements, RAt1, at two wavelengths, $\lambda 1$ and $\lambda 2$, $\lambda 1$ being selected at 293 nm and $\lambda 2$, the "blanking wavelength", being selected at 700 nm. A few seconds after t1, usually between 10 and 25 seconds later, at a time tr, known volumes of reagents and purified water are introduced into the cuvette 18. FIG. 6 shows the effect upon monitored reaction absorption as being a sharp increase followed by a gradual decrease starting at the time ts of addition of sample to the previously combined assay reagent(s) and water. Ultrasonic mixing using pulsed applications of energy has again been found to be effective in providing a high degree of mixing uniformity. It has been experimentally determined that a first ultrasonic mixing of reagent and water using mixer 31 when conducted over a period of about one-half second in a uniformly spaced series of ten pulsed applications of ultrasonic energy for about 5 msec using a voltage level of 325 volts produces satisfactorily uniform mixing of reagent(s) and water. A sample to be analyzed for the presence of uric acid is added at time ts about 60 seconds after tr and this addition is followed by pulsed ultrasonic mixing using mixer 30, in this uric acid assay for a period of about one-half second in a uniformly spaced series of five 40 msec pulsed applications of ultrasonic energy at a voltage level of about 375 volts, the times and ultrasonic energy levels being empirically determined to produce a uniformity of mixing that will yield "analytically correct measurements". In commercial applications of such a uric acid analysis, as illustrated in FIG. 6, an endpoint reaction absorbance measurement, RAt3, attributable to the cuvette 18 plus the first reagent and water and sample is made at time t3, in this instance after an elapsed time of about 300 seconds following sample addition. The amount of time allowed to lapse prior to making an endpoint measurement at t3 is empirically selected so as to be sufficient to allow the reaction to be essentially fully completed after addition of sample into the cuvette 18. The same Endpoint Reaction Absorbance is made as in the prior example, again using Formula 1.

Figure 8:
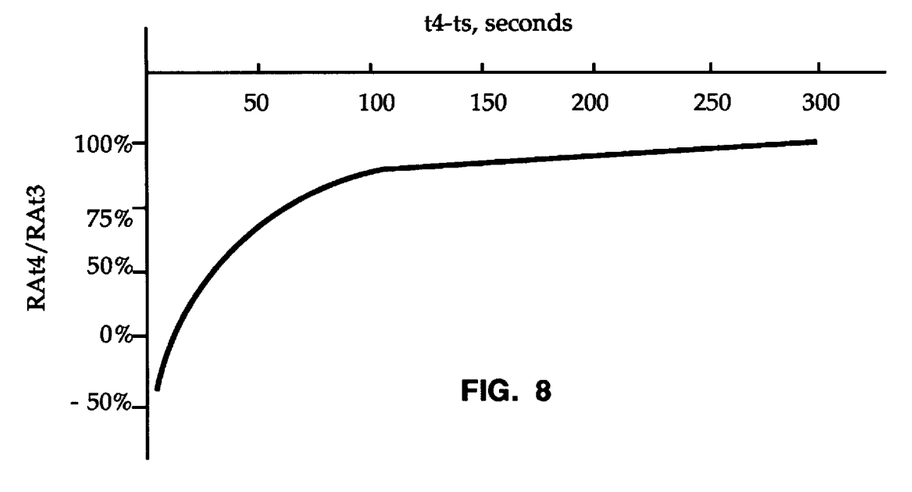
FIG. 8 is a graphical representation of signal absorption ratios typical of sufficient mixing of sample and reagents exemplary of the present invention for the assay of FIG. 6.

As previously described in the case of an "positive absorption" reaction, it has also been found that with "negative absorption" assays, the reaction absorption value determined during the time of the reaction can be used in comparison to the final endpoint reaction absorption value to ascertain the degree of mixing efficiency. As shown in FIG. 6, as the reaction nears an endpoint completion at a time t4 selected to be about 50–70% of the time interval between ts and t3, a new reaction absorption measurement RAt4 made at time t4, can be compared to the endpoint reaction absorption measurement RAt3 and the ratio of RAt4 to RAt3 used to determine the adequacy of mixing of the sample analyzed using reaction absorption measurements. As illustrated in FIG. 8 and described later, it has been determined that if time t4 is selected within this range, and if the ratio of RAt4 to RAt3 is in a range from about 98% to 102%, then uniform mixing of the reagent, water and sample is sufficiently uniform so as to achieve analytically acceptable uniformity of mixing. The date were determined on a group of five different samples.

Figure 7:
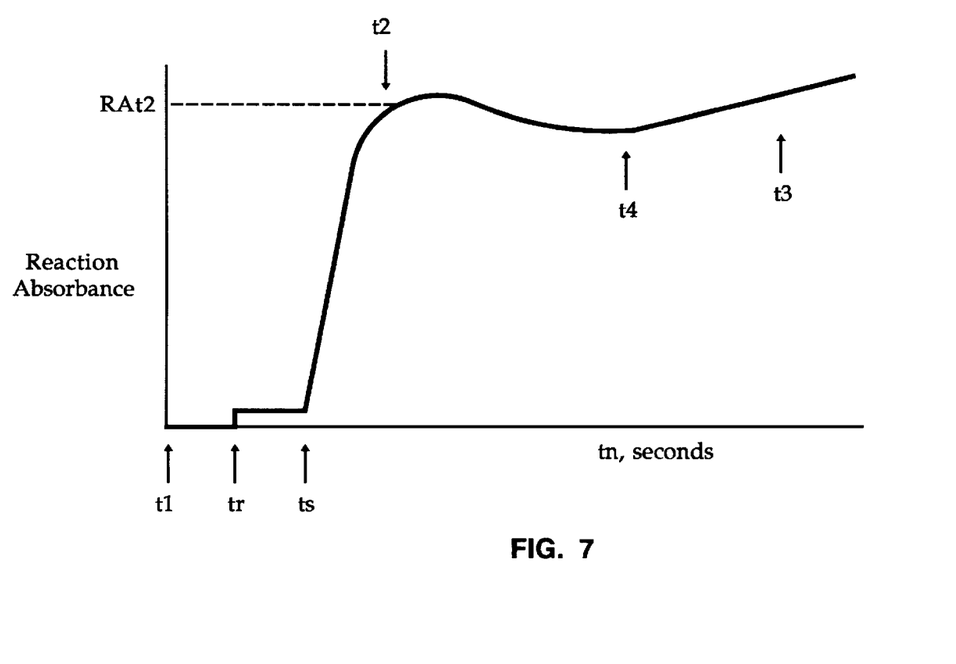
FIG. 7 is a graphical representation of events in a second type of end-point analytical assay having analytically insufficient mixing.

In contrast to FIG. 6, FIG. 7 illustrates an "insufficient mixing" situation in the same "negative absorption" assay for uric acid at different time values for t4 where t3 is 300 sec. and where the results of analytically unacceptable mixing when either: (1) no ultrasonic energy was applied by mixer 30 to a reaction solution containing uric acid in solution with uricase; or when, (2) ultrasonic energy was applied by mixer 30 for one 20 msec pulsed application of ultrasonic energy at a voltage level of about using a voltage level of 375 volts, an energy level know to be about 10% of the normal level of energy known to produce an analytically acceptable uniformity of mixing.

Figure 9:
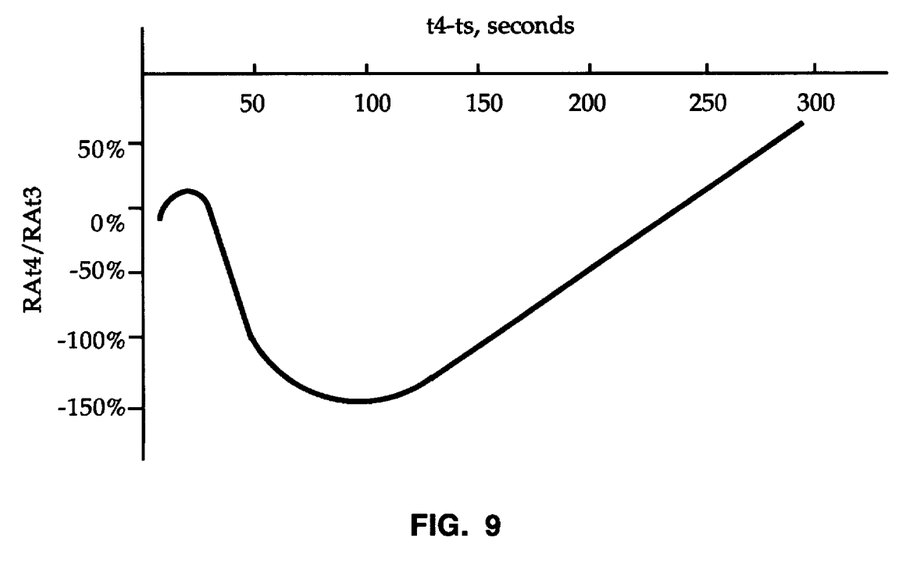
FIG. 9 is a graphical representation of signal absorption ratios typical of insufficient mixing of sample and reagents exemplary of the present invention for the assay of FIG. 7.

FIG. 8 shows a series of ratios between RAt4 and RAt3 determined as illustrated for the "negative absorption" assay of FIG. 6 for uric acid using ultrasonic mixing energy levels known to yield "analytically correct measurements". In this instance of a "negative absorption" analytical assay, the time dependent ratios between RAt4 and RAt3 determined at different times t4 during a reaction make it clear that the ratio between RAt4 and RAt3 at a time t4 equal to about 50–70% of the difference between ts and endpoint t3 in a range from about 98% to 102%. In contrast, FIG. 9 shows the series of ratios between RAt4 and RAt3 illustrated in FIG. 7 at ultrasonic energy levels know to be about 10% of the normal level of energy known to produce an analytically acceptable uniformity of mixing. For these "insufficient mixing" instances, and as is also found in the case for the "positive absorption" glucose assay, the difference between RAt4 and RAt3 at time t4 equal to about 50–70% of the difference between ts and endpoint t3 is generally found to be less than about 95%. In some exceptional instances, the ratio between RAt4 and RAt3 has been measured to be higher than about 95% but in these instances, although not fully understood, the measurements are found to have an abnormally large range of values.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. Within a chemical analyzer, a method for determining the reliability of analytical tests, the method comprising:
ensuring that a uniform mixture has been established within a liquid solution in a reaction vessel containing at least one reagent and liquid sample by:
measuring a first amount of light absorbed within the solution a first time after the reaction begins;
measuring a second amount of light absorbed within the solution at a second time at the completion of the reaction; and,
requiring that the ratio between the first and second measured amounts of absorbed light be greater than a predetermined value.

2. The method of claim 1 wherein the first time represents an amount of time in the range of about 50–70 percent of the difference between the time the reaction begins and the time of completion of the reaction.

3. The method of claim 1 wherein the predetermined value is about ninety-five percent.

4. The method of claim 1 wherein the assay is an assay in which light absorption increases during the measurement procedure.

5. The method of claim 4 wherein the assay is an assay for glucose.

6. The method of claim 1 wherein the assay is an assay in which light absorption decreases during the measurement procedure.

7. The method of claim 6 wherein the assay is an assay for uric acid.

8. The method of claim 1 wherein measuring the amount of light absorbed within the solution comprises a light measurement made at two wavelengths, the first wavelength characteristic of the reaction of the sample and reagents, and the second wavelength characteristic of the reaction vessel and interfering substances within the vessel.

9. Within a chemical analyzer, a method for detecting the unreliability of analytical tests, the method comprising:
determining that a uniform mixture has not been established within a liquid solution in a reaction vessel containing at least one reagent and liquid sample by:
measuring a first amount of light absorbed within the solution a first time after the reaction begins;
measuring a second amount of light absorbed within the solution at a second time at the completion of the reaction; and,
observing that the ratio between the first and second measured amounts of absorbed light is less than a predetermined value.

10. The method of claim 9 wherein the first time represents an amount of time in the range of about 50–70 percent of the difference between the time the reaction begins and the time of completion of the reaction.

11. The method of claim 9 wherein the predetermined value is about ninety-five percent.

12. The method of claim 9 wherein the assay is an assay in which light absorption increases during the measurement procedure.

13. The method of claim 12 wherein the assay is an assay for glucose.

14. The method of claim 9 wherein the assay is an assay in which light absorption decreases during the measurement procedure.

15. The method of claim 14 wherein the assay is an assay for uric acid.

16. The method of claim 9 wherein the assay is an assay for glucose or uric acid.

17. The method of claim 9 wherein measuring the amount of light absorbed within the solution comprises a light measurement made at two wavelengths, the first wavelength characteristic of the reaction of the sample and reagents, and the second wavelength characteristic of the reaction vessel and interfering substances within the vessel.

* * * * *